United States Patent
Hofman et al.

(10) Patent No.: US 11,315,689 B2
(45) Date of Patent: *Apr. 26, 2022

(54) INTERACTIVE GRAPHICAL SYSTEM FOR ESTIMATING BODY MEASUREMENTS

(71) Applicant: Microsoft Technology Licensing, LLC, Redmond, WA (US)

(72) Inventors: Jake M. Hofman, New York, NY (US); Daniel G. Goldstein, New York, NY (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 254 days.

This patent is subject to a terminal disclaimer.

(21) Appl. No.: 16/658,411

(22) Filed: Oct. 21, 2019

(65) Prior Publication Data

US 2020/0050606 A1    Feb. 13, 2020

Related U.S. Application Data

(63) Continuation of application No. 14/921,110, filed on Oct. 23, 2015, now Pat. No. 10,521,429.

(Continued)

(51) Int. Cl.
| | |
|---|---|
| *G16H 50/30* | (2018.01) |
| *G06Q 30/06* | (2012.01) |
| *G06F 3/04842* | (2022.01) |
| *G06N 7/00* | (2006.01) |
| *G06F 16/2455* | (2019.01) |
| *G16H 50/50* | (2018.01) |
| *G16H 20/60* | (2018.01) |
| *G16H 10/60* | (2018.01) |

(52) U.S. Cl.
CPC ......... *G16H 50/30* (2018.01); *G06F 3/04842* (2013.01); *G06F 16/2455* (2019.01); *G06N 7/005* (2013.01); *G16H 50/50* (2018.01); *G06Q 30/0643* (2013.01); *G16H 10/60* (2018.01); *G16H 20/60* (2018.01)

(58) Field of Classification Search
CPC .......... G06Q 30/0631; G06Q 30/0621; G06Q 30/0643; G16H 20/60; G16H 10/60
See application file for complete search history.

(56) References Cited

U.S. PATENT DOCUMENTS

| | | | |
|---|---|---|---|
| 2010/0111370 A1* | 5/2010 | Black | G06K 9/00369 382/111 |
| 2016/0035061 A1* | 2/2016 | Gadre | G06T 19/00 345/473 |
| 2016/0275600 A1* | 9/2016 | Adeyoola | G06T 11/001 |

* cited by examiner

*Primary Examiner* — Jonathan Durant
(74) *Attorney, Agent, or Firm* — Faegre Drinker Biddle & Reath LLP (57) ABSTRACT

Utilizing graphical elements representing human bodies to estimate physical measurements of a user is described. In at least one example, a service provider can access a database storing a plurality of data items. The service provider can cause a set of data items of the plurality of data items to be presented to the user. Data items in the set of data items are associated with at least one graphical element representing a human body with individual magnitudes corresponding to individual dimensions of a plurality of dimensions. The service provider can receive data indicating a selection of a data item associated with a first magnitude associated with a first dimension and a second magnitude associated with a second dimension. The service provider can estimate physical measurements associated with the user based partly on a first magnitude and/or the second magnitude.

20 Claims, 4 Drawing Sheets

Related U.S. Application Data

(60) Provisional application No. 62/173,120, filed on Jun. 9, 2015.

```
┌─────────────────────────────────────────────┐
│  ACCESS USER DATA AND DATA ASSOCIATED WITH USER │
│                 SELECTIONS                    │
│                     402                       │
└─────────────────────────────────────────────┘
                      │
                      ▼
┌─────────────────────────────────────────────┐
│     ACCESS ESTIMATED PHYSICAL MEASUREMENTS    │
│                     404                       │
└─────────────────────────────────────────────┘
                      │
                      ▼
┌─────────────────────────────────────────────┐
│             TRAIN PREDICTIVE MODEL            │
│                     406                       │
└─────────────────────────────────────────────┘
```

FIG. 4

INTERACTIVE GRAPHICAL SYSTEM FOR ESTIMATING BODY MEASUREMENTS

RELATED APPLICATIONS

This application is a continuation of U.S. application Ser. No. 14/921,110, filed on Oct. 23, 2015, which claims the benefit of U.S. Provisional Application No. 62/173,120 filed on Jun. 9, 2015, the entire contents of which are incorporated herein by reference.

BACKGROUND

Physical measurements of human bodies are useful for various purposes. For instance, health professionals use physical measurements to calculate body mass index (BMI). BMI is a measurement of a person's body fat based on the person's height and weight that can be used to determine whether the person is underweight, overweight, obese, etc. BMI, waist measurement, etc. can be useful for determining whether persons are at risk for various diseases. Additionally, many apparel companies use physical measurements to determine sizes and fits of garments. Collecting physical measurements, however, is time consuming. Additionally, persons can find themselves in situations where tools used for determining physical measurements are not accessible, such as in the developing world, in online applications, etc.

SUMMARY

This disclosure describes utilizing graphical elements representing human bodies to estimate physical measurements of a person. In at least one example, a service provider can access a database storing a plurality of data items. The service provider can cause a set of data items of the plurality of data items to be presented to the user. Data items in the set of data items are associated with at least one graphical element representing a human body with individual magnitudes corresponding to individual dimensions of a plurality of dimensions. The service provider can receive data indicating a selection of a data item associated with a first magnitude associated with a first dimension and a second magnitude associated with a second dimension. The service provider can estimate physical measurements associated with the user based partly on a first magnitude and/or the second magnitude.

This Summary is provided to introduce a selection of concepts in a simplified form that are further described below in the Detailed Description. This Summary is not intended to identify key or essential features of the claimed subject matter, nor is it intended to be used to limit the scope of the claimed subject matter.

BRIEF DESCRIPTION OF THE DRAWINGS

The Detailed Description is set forth with reference to the accompanying figures, in which the left-most digit of a reference number identifies the figure in which the reference number first appears. The use of the same reference numbers in the same or different figures indicates similar or identical items or features.

DETAILED DESCRIPTION

This disclosure describes utilizing graphical elements representing human bodies to estimate physical measurements of a person. Technologies described herein can enable physical measurements to be estimated without requiring access to measuring devices such as scales, measuring tapes, body fat meters, body fat calipers, etc. That is, the technologies described herein include estimating physical measurements when few or no measuring devices are available using data items associated with graphical elements representing human bodies and inputs associated with the data items. The technologies described herein can be used to replace, assist, and/or supplement technologies currently implemented to determine physical measurements using various measuring devices (e.g., scales, tape measures, etc.).

For illustrative purposes, a physical measurement represents a definite magnitude of a physical quantity that is used as a standard for quantifying a dimension of a part of the human body and/or a characteristic of the human body. Physical measurements can be associated with any system of units (e.g., metric system, United States customary measurement system, natural unit system, etc.). A physical measurement can be a definite magnitude of a physical quantity of dimension of a user's neck (e.g., circumference, length, width, etc.), upper arm (e.g., circumference, length, width, etc.), chest (e.g., circumference, length, width, etc.), bust (e.g. circumference, etc.), waist (e.g., circumference, length, width, etc.), hips (e.g., circumference, length, width, etc.), thigh (e.g., circumference, length, width, etc.), calf (e.g., circumference, length, width, etc.), leg (e.g., circumference, length, width, etc.), arm (e.g., circumference, length, width, etc.), etc. Physical measurements can include measurements of a user's height, weight, body fat percentage, etc.

Physical measurements can also include measurements that are determined based on other physical measurements, such as BMI, as described above. BMI is an estimate of a user's body fat based on the user's height and weight that can be used to determine whether a user is underweight, overweight, obese, etc. BMI can be useful for determining whether users are at risk for various diseases. BMI is determined based on dividing a user's mass in kilograms by the square of the user's height in meters, or by multiplying a user's mass in pounds by 703 and dividing the product by the square of the user's height in inches.

Technologies described herein cause one or more sets of data items to be presented to a user via an interface of a device that can be associated with the user (e.g. a user device). Each data item can be associated with at least one graphical element representing a human body having individual magnitudes of individual physical measurements corresponding to individual dimensions. That is, a data item can be associated with at least one graphical element that graphically represents a human body that has proportions that are consistent with a real human body having individual physical measurements corresponding to individual magnitudes. The graphical elements can be graphical representations of human bodies, such as two-dimensional or three-dimensional graphical representations of human bodies.

As described above, the technologies described herein can cause one or more sets of data items to be presented to a user via an interface of a device that can be associated with the user (e.g. a user device). A set of data items includes one or more data items. In at least one example, a set of data items can be a subset of data items from a database of data items. Individual data items in a set of data items can be associated with at least one graphical element representing a human body with magnitudes associated with physical measurements that are different from other individual data items in the set of data items. For instance, each of the data items in a set of data items can be associated with at least one graphical element representing a human body with magnitudes including a first magnitude associated with a first dimension and a second magnitude associated with a second dimension. In at least one example, the first magnitude can be the same for all data items in the set of data items and the second magnitude can be different for each data item in the set of data items. For instance, a set of data items can include data items associated with at least one graphical element that represents human bodies that have same BMIs and different waist measurements. In some examples, the magnitudes represented by graphical representations in each data item can differ from other data items in a set of data items by a single magnitude associated with a single dimension. That is, all of the magnitudes associated with all of the dimensions can be the same except for one magnitude associated with one dimension. For instance, a set of data items can include data items each associated with at least one graphical element that represents a human body that has all of the same magnitudes as the other data items in the set of data items except that each data item in the set of data items is associated with at least one graphical element that represents a human body with a different waist measurement.

The user can select a data item that is associated with graphical elements representing human bodies that look most like themselves, or in some examples, another person (e.g., a friend, a family member, a suspected criminal/person of interest, etc.), as described below. The service provider can receive data indicating the user selection. Based at least in part on receiving the data associated with the user selection, the service provider can retrieve second (or subsequent) sets of data items. In at least one example, at least one of the magnitudes represented by individual data items in the second (or any subsequent) set of data items can be based on the magnitudes represented by the data item selected by the user from the previous set of data items. As a non-limiting example, if the second set of the data items includes individual data items that are associated with one or more graphical elements representing human bodies that have different BMIs, the individual data items can be associated with one or more graphical elements representing human bodies with a same waist measurement based on the waist measurement corresponding to the data item selected by the user in the first set of data items. The technologies described herein leverage the user selection (e.g., input) and other user data to estimate physical measurements of the user (or the other person). That is, the technologies described herein can estimate physical measurements such as waist measurement, BMI, etc., without needing access to measuring devices.

Estimating physical measurements can be useful in various applications including, but not limited to, health and/or disease prevention applications, video gaming applications, online apparel shopping applications, law enforcement applications, etc. For instance, health and/or fitness products (e.g., Microsoft Band, Fitbit®, etc.) can utilize the technologies described herein to prompt users to select data items associated with graphical elements representing human bodies that they believe look most like themselves and to leverage the users' selections overtime to estimate how the users' bodies are changing and/or changes in physical measurements. This data can be correlated with other data collected from a health and/or fitness application (e.g., activity data, heart rate data, etc.) to enable users to track progress and enable users to see what activities, etc. impact their health and/or fitness. In other examples, the technologies described herein can be useful for disease identification and prevention. As described above, health professionals utilize physical measurements to predict whether a user is underweight, overweight, obese, etc., whether users are at risk for various diseases (e.g., cardiac, hypertension, diabetes, etc.), etc. Accordingly, the technologies described herein can be utilized to identify and prevent diseases without relying on measuring devices.

In additional or alternative examples, the technologies described herein can be utilized by gaming products and/or applications to generate realistic depictions of how users appear (i.e., avatars). For instance, the technologies described herein can prompt a user to select data items associated with graphical elements representing human bodies that they believe look most like themselves and can leverage the user's selections to generate realistic looking avatars. In other examples, the technologies described herein can be useful in online shopping applications. For instance, a user may not know his or her physical measurements. Accordingly, the technologies described herein can prompt a user to select data items associated with graphical elements representing human bodies that they believe look most like themselves and can leverage the user's selections to estimate physical measurements for recommending sizes of apparel. Additionally or alternatively, a user can be shopping online for a gift for another user (e.g., family member, friend, etc.) and he or she may not know the other user's physical measurements and/or size. Accordingly, the technologies described herein can prompt a user to select data items associated with graphical elements representing human bodies that they believe look most like the other user and can leverage the user's selections to estimate physical measurements for recommending sizes of apparel.

In yet another example, the technologies described herein can be useful for identifying suspected criminals/persons of interest and can therefore be useful for law enforcement applications. For instance, the technologies described herein can prompt a user to select data items associated with graphical elements representing human bodies that they believe look most like a suspect and can leverage the user's selections to estimate physical measurements for the suspect. The technologies described herein can also be used for searching through databases of data items associated with one or more graphical elements of known criminals.

Illustrative Environments

Figure 1:
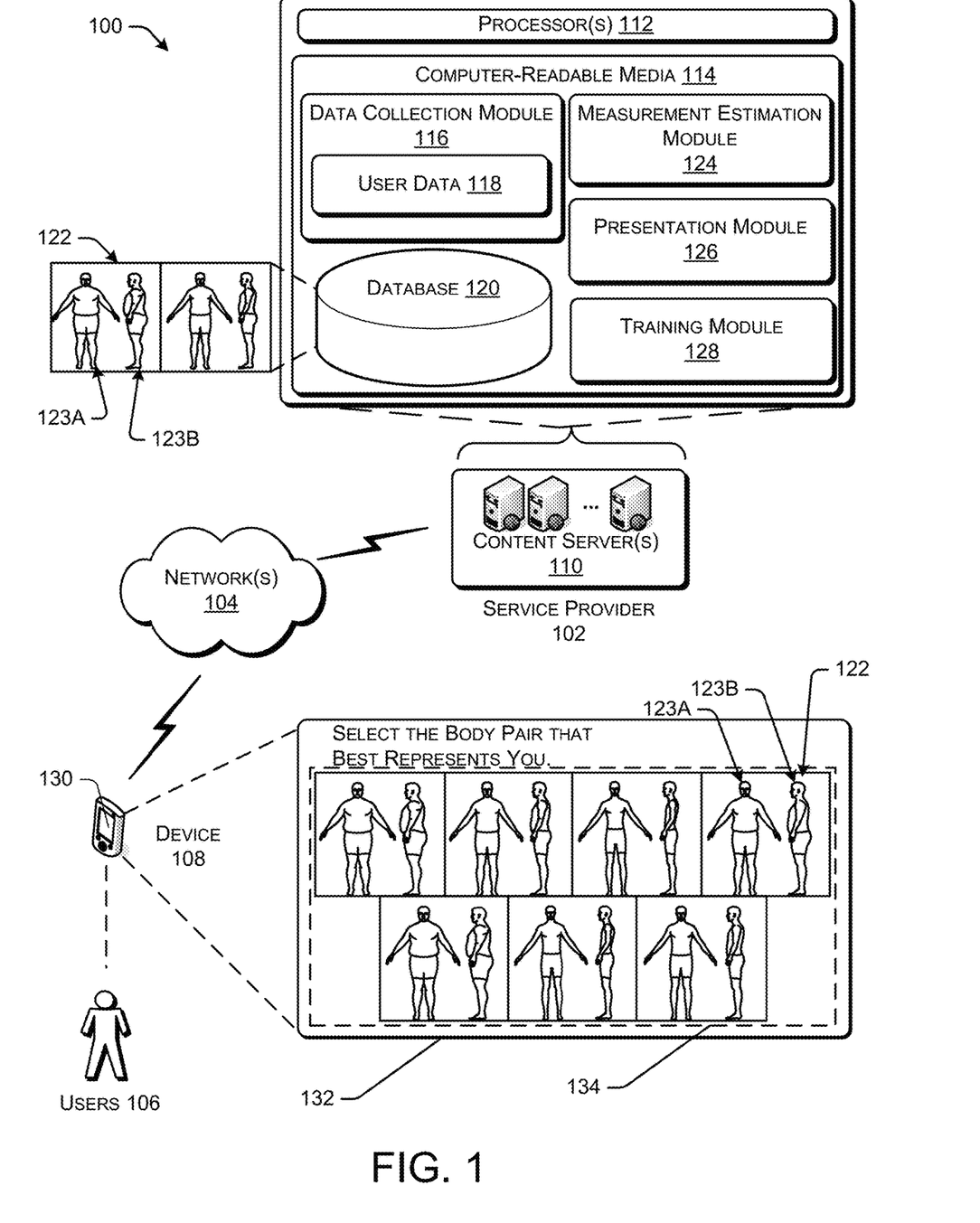
FIG. 1 is a schematic diagram showing an example environment for utilizing data items associated with graphical elements representing human bodies to estimate physical measurements.

FIG. 1 is a schematic diagram showing an example environment 100 for utilizing data items associated with one or more graphical elements representing human bodies to estimate physical measurements. More particularly, the example environment 100 can include a service provider 102, one or more network(s) 104, one or more users 106, and one or more devices 108 associated with the one or more users 106.

The service provider 102 can be any entity, server(s), platform, etc., that facilitates presenting one or more sets of data items each associated with one or more graphical elements representing human bodies and leveraging inputs associated with individual data items to estimate physical measurements associated with users 106 and/or other persons (e.g., friends, family members, suspected criminals/persons of interest, etc.), as described above. The service provider 102 can be implemented in a non-distributed computing environment or can be implemented in a distributed computing environment, possibly by running some modules on devices 108 or other remotely located devices. As shown, the service provider 102 can include one or more server(s) 110, which can include one or more processing unit(s) 112 and computer-readable media 114, such as memory. In various examples, the service provider 102 can access data items associated with one or more graphical elements representing human bodies from a database, cause the data items to be presented to a user 106 in one or more sets of data items, receive data associated with user selection of individual data items, and leverage the magnitudes associated with the individual data items selected by the user 106 and other user data to estimate physical measurements associated with the user 106 and/or another person, as described above. The technologies described herein enable the service provider 102 to search and retrieve data items that are stored in the database and estimate physical measurements based on said data items more efficiently (i.e., faster) than if humans were involved, as described below.

In some examples, the network(s) 104 can be any type of network known in the art, such as the Internet. Moreover, the devices 108 can communicatively couple to the network(s) 104 in any manner, such as by a global or local wired or wireless connection (e.g., local area network (LAN), intranet, etc.). The network(s) 104 can facilitate communication between the server(s) 110 and the devices 108 associated with the users 106.

In some examples, the users 106 can operate corresponding devices 108 (e.g., user devices) to perform various functions associated with the devices 108, which can include one or more processing unit(s), computer-readable storage media, and a display 130. Device(s) 108 can represent a diverse variety of device types and are not limited to any particular type of device. Examples of device(s) 108 can include but are not limited to stationary computers, mobile computers, embedded computers, or combinations thereof. Example stationary computers can include desktop computers, work stations, personal computers, thin clients, terminals, game consoles, personal video recorders (PVRs), set-top boxes, or the like. Example mobile computers can include laptop computers, tablet computers, wearable computers, implanted computing devices, telecommunication devices, automotive computers, portable gaming devices, media players, cameras, or the like. Example embedded computers can include network enabled televisions, integrated components for inclusion in a computing device, appliances, microcontrollers, digital signal processors, or any other sort of processing device, or the like.

Examples support scenarios where device(s) that can be included in the one or more server(s) 110 can include one or more computing devices that operate in a cluster or other clustered configuration to share resources, balance load, increase performance, provide fail-over support or redundancy, or for other purposes. Device(s) included in the one or more server(s) 110 can represent, but are not limited to, desktop computers, server computers, web-server computers, personal computers, mobile computers, laptop computers, tablet computers, wearable computers, implanted computing devices, telecommunication devices, automotive computers, network enabled televisions, thin clients, terminals, game consoles, gaming devices, work stations, media players, digital video recorders (DVRs), set-top boxes, cameras, integrated components for inclusion in a computing device, appliances, or any other sort of computing device.

Device(s) that can be included in the one or more server(s) 110 can include any type of computing device having one or more processing unit(s) 112 operably connected to computer-readable media 114 such as via a bus, which in some instances can include one or more of a system bus, a data bus, an address bus, a PCI bus, a Mini-PCI bus, and any variety of local, peripheral, and/or independent buses. Executable instructions stored on computer-readable media 114 can include, for example, a data collection module 116, storing user data 118, a database 120, storing data items 122 associated with one or more graphical elements 123A, 123B, etc., representing human bodies, a measurement estimation module 124, a presentation module 126, a training module 128, and other modules, programs, or applications that are loadable and executable by processing units(s) 112.

Alternatively, or in addition, the functionality described herein can be performed, at least in part, by one or more hardware logic components such as accelerators. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip Systems (SOCs), Complex Programmable Logic Devices (CPLDs), etc. Device(s) that can be included in the one or more server(s) 110 can further include one or more input/output (I/O) interface(s) coupled to the bus to allow device(s) to communicate with other devices such as input peripheral devices (e.g., a keyboard, a mouse, a pen, a game controller, a voice input device, a touch input device, gestural input device, and the like) and/or output peripheral devices (e.g., a display, a printer, audio speakers, a haptic output, and the like). Such network interface(s) can include one or more network interface controllers (NICs) or other types of transceiver devices to send and receive communications over a network. For simplicity, some components are omitted from the illustrated environment.

Processing unit(s) 112 can represent, for example, a CPU-type processing unit, a GPU-type processing unit, a Field-programmable Gate Array (FPGA), another class of Digital Signal Processor (DSP), or other hardware logic components that can, in some instances, be driven by a CPU. For example, and without limitation, illustrative types of hardware logic components that can be used include Application-Specific Integrated Circuits (ASICs), Application-Specific Standard Products (ASSPs), System-on-a-chip systems (SOCs), Complex Programmable Logic Devices (CPLDs), etc. In various examples, the processing unit(s) 112 can execute one or more modules and/or processes to cause the server(s) 110 to perform a variety of functions, as set forth above and explained in further detail in the following disclosure. Additionally, each of the processing unit(s) 112 can possess its own local memory, which also can store program modules, program data, and/or one or more operating systems.

In at least one configuration, the computer-readable media 114 of the server(s) 110 can include components that facilitate interaction between the service provider 102 and the users 106. The components can represent pieces of code executing on a computing device. For example, the computer-readable media 114 can include the data collection module 116, the database 120, the measurement estimation module 124, the presentation module 126, the training module 128, etc. In at least some examples, the modules (116, 120, 126, 128, etc.) can be implemented as computer-readable instructions, various data structures, and so forth via at least one processing unit(s) 112 to configure a device to execute instructions and to perform operations implementing generating response templates that correspond to ontological elements. Functionality to perform these operations can be included in multiple devices or a single device.

The computer-readable media 114 can also include the database 120 for storing data items 122 associated with one or more graphical elements 123A, 123B, etc. representing human bodies, as described above. As a non-limiting example, FIG. 1 shows example data items 122 associated with one or more graphical elements 123A, 123B, etc. representing human bodies having a set of magnitudes. That is, the data items 122 can be associated with one or more graphical elements 123A, 123B, etc. that graphically represent human bodies that have proportions that are consistent with a human body having a set of physical measurements whereby each individual physical measurement corresponds to an individual magnitude, as described above. Each graphical element 123A, 123B, etc. can be associated with a different view of the human body having the set of magnitudes. As a non-limiting example, FIG. 1 shows a data item 122, where one of the graphical elements 123A is a frontal view of a human body having a set of magnitudes and the other graphical element 124B is a profile view of the human body having the set of magnitudes. The database of data items 122 can include different data items 122 based on different demographics (e.g., nationalities, ethnicities, genders, ages, etc.).

Depending on the exact configuration and type of the server(s) 110, the computer-readable media 114 can include computer storage media and/or communication media. Computer storage media can include volatile memory, non-volatile memory, and/or other persistent and/or auxiliary computer storage media, removable and non-removable computer storage media implemented in any method or technology for storage of information such as computer readable instructions, data structures, program modules, or other data. Computer memory is an example of computer storage media. Thus, computer storage media includes tangible and/or physical forms of media included in a device and/or hardware component that is part of a device or external to a device, including but not limited to random-access memory (RAM), static random-access memory (SRAM), dynamic random-access memory (DRAM), phase change memory (PRAM), read-only memory (ROM), erasable programmable read-only memory (EPROM), electrically erasable programmable read-only memory (EEPROM), flash memory, compact disc read-only memory (CD-ROM), digital versatile disks (DVDs), optical cards or other optical storage media, miniature hard drives, memory cards, magnetic cassettes, magnetic tape, magnetic disk storage, magnetic cards or other magnetic storage devices or media, solid-state memory devices, storage arrays, network attached storage, storage area networks, hosted computer storage or any other storage memory, storage device, and/or storage medium that can be used to store and maintain information for access by a computing device.

In contrast, communication media can embody computer readable instructions, data structures, program modules, or other data in a modulated data signal, such as a carrier wave, or other transmission mechanism. The term "modulated data signal" means a signal that has one or more of its characteristics set or changed in such a manner as to encode information in the signal. Such signals or carrier waves, etc. can be propagated on wired media such as a wired network or direct-wired connection, and/or wireless media such as acoustic, RF, infrared and other wireless media. As defined herein, computer storage media does not include communication media. That is, computer storage media does not include communications media consisting solely of a modulated data signal, a carrier wave, or a propagated signal, per se.

The data collection module 116 can receive data associated with users 106 (e.g., user data 118) from the users 106 and/or on behalf of the users 106 and/or access data associated with users 106 via third party sources and systems (e.g., social networks, professional networks, etc.). In some examples, users 106 can input user data 118 when they set up a user account or profile for interacting with the service provider 102, an application, a website, etc., in response to a prompt for user data 118, etc. In at least one example, the presentation module 126 can cause one or more user interfaces to be presented to the user 106. The one or more user interfaces can provide functionality for the user 106 to input information. The user 106 can input personal information including, but not limited to, gender, age, physical measurements, etc., to the data collection module 116.

In other examples, the data collection module 116 can receive data from devices such as input peripheral devices (e.g., sensors, cameras, and the like). For instance, a camera and/or sensor can determine a user's 106 height and provide data indicating the user's 106 height to the data collection module 116. In additional or alternative examples, the data collection module 116 can infer user data 118 based on user interactions with the service provider 102. For instance, a user 106 can select a data item 122 representative of a female out of a set of data items 122 representing both genders. Accordingly, the data collection module 116 can infer that the user 106 is a female. In some examples, the data collection module 116 can access user data 118 from third party sources and systems (e.g., social networks, professional networks, etc.). The user data 118 can be mapped to and/or otherwise associated with profiles that correspond to individual users 106. The profiles that correspond to the individual users 106 can be stored in a database associated with the user data 118 and/or some other data repository.

The data collection module 116 can also receive data associated with user selections of data items 122 from sets of data items that are presented to the user 106. In at least one example, the presentation module 126 can cause sets of data items to be presented to the user 106 via one or more personalized user interfaces, described below, that provide functionality for the user 106 to select individual data items 122 of the set of data items 122. The user 106 can interact with the data items 122 that are presented via the user interface utilizing various mechanisms. In some examples, the user 106 can interact with the data items 122 via input peripheral devices (e.g., a keyboard, a mouse, a pen, a game controller, a voice input device, a touch input device, gestural input device, cameras, sensors, and the like), touch input, etc. The data collection module 116 can analyze the data to determine the magnitudes that correspond to each of the data items 122 selected by the user 106. The data collection module 116 can log each input and associate the logs with a profile corresponding to the user 106 in the database associated with the user data 118 and/or other data repository. Each log can correspond to a set of magnitudes that are represented by the data item 122 that the user 106 selected.

The database 120 stores data items 122, as described above. In at least one example, the data items 122 can be associated with one or more graphical elements that represent human bodies having different genders, heights, waist measurements, BMIs, etc. The data items 122, as described above, can be associated with one or more graphical elements 123A, 123B, etc. that represent human bodies. The one or more graphical elements 123A, 123B, etc. associated with each data item 122 each represent a human body having a same set of magnitudes, as described above. The data items 122 illustrated in FIG. 1 are examples of data items 122 that can be presented to users 106, and any other presentation or configuration can be used.

The database 120 can be associated with an index, such as a lookup table, where the data items 122 can be indexed based on magnitudes and/or other characteristics (e.g., gender, etc.). In a non-limiting example, the data items 122 can be indexed by gender, height, dimension (e.g., waist measurement, BMI, etc.), etc. The index can expedite the time required to retrieve data items 122 from the database 120 and reduce runtime computations associated with retrieving the data items 122. As a result, the index enables the data collection module 116 and/or presentation module 126 to retrieve data items 122 that are stored in the database 120 more efficiently (i.e., faster) then if humans were involved.

The measurement estimation module 124 accesses user data 118 and logs associated with data associated with selections of data items 122. In at least one example, as described above, the user data 118 and logs can be mapped to and/or otherwise associated with a profile corresponding to a user 106 that is stored in the database associated with the user data 118. In such examples, the measurement estimation module 124 can access the profile stored in the database for estimating physical measurements of a user 106. The measurement estimation module 124 utilizes the user data 118 and magnitudes associated with the logs to estimate physical measurements associated with the user 106.

The measurement estimation module 124 can utilize one or more predictive models to compute the estimated physical measurements. The one or more predictive models can change based on the dimensions to be estimated, population of users, demographic of the population of users, etc. Predictive Models 1 and 2, reproduced below, are non-limiting examples of predictive models that the measurement estimation module 124 can use for computing the estimated physical measurements (e.g., BMI and waist measurement, respectively). In each of the predictive models below, the weights ($\beta_x$) are based at least in part on training the predictive model described below using user data 118, including previous inputs. Predictive Model 1 can be used to predict a user's 106 BMI (in kilograms/meters$^2$) and Predictive Model 2 can be used to predict a user's 106 waist measurement (in millimeters). The "selected_waist" and "selected_bmi" variables are determined from a most recent (e.g., the last) data item 122 selected by the user 106.

predicted_bmi=$\beta_0$+$\beta_1$is_male+$\beta_2$selected_bmi+$\beta_3$ selected_waist+$\beta_4$ selected_waist:selected_bmi PREDICTIVE MODEL 1 predicted_waist=$\beta_0$+$\beta_1$is_male+$\beta_2$ selected_bmi+$\beta_3$ selected_waist+$\beta_4$ selected_waist:selected_bmi PREDICTIVE MODEL 2

In both examples, selected_waist:selected_bmi denotes the product of the selected_waist and selected_bmi.

The presentation module 126 can generate user interfaces that provide various functionalities, as described above and also below. The presentation module 126 can cause a user interface to be presented to users 106 utilizing any communication channel, such as an e-mail message, a site (e.g., website) associated with the service provider 102, a text message, a social network site, an application that is associated with the service provider 102 and that resides on device(s) 108 of the users 106, etc. In at least one example, the presentation module 126 can generate a user interface that includes a set of data items (e.g., a subset of the data items 122 stored in the database 120). The user interface can be configured to receive input from the user 106 and/or on behalf of the user 106 indicating a selection of at least one data item 122 in the set of data items. The presentation module 126 can cause the user interface to be presented on a display 130 of a device 108.

A non-limiting example of a user interface 132 is illustrated in FIG. 1. User interface 132 includes a set of data items 134, as shown by the dashed lines. The set of data items 134 includes individual data items 122, as described above. In FIG. 1, the data items 122 are associated with two graphical elements 123A and 123B that each represent a human body having a set of magnitudes (i.e., pairs of graphical elements).

In additional and/or alternative examples, the presentation module 126 can generate a user interface that prompts users 106 for user information such as gender, height, etc., and/or a user interface that presents estimated physical measurements to the users 106.

The training module 128 can train the predictive model based at least in part on user data 118, including determined physical measurements (e.g., physical measurements determined using a measuring device), data associated with user selections, and estimated physical measurements, as described in FIG. 4 below. The predictive model can include a multiple regression model, etc., as described above in the non-limiting examples of Predictive Model 1 and Predictive Model 2.

Example Processes

The processes described in FIGS. 2-4 below are illustrated as a collection of blocks in a logical flow graph, which represent a sequence of operations that can be implemented in hardware, software, or a combination thereof. In the context of software, the blocks represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the processes.

Figure 2:
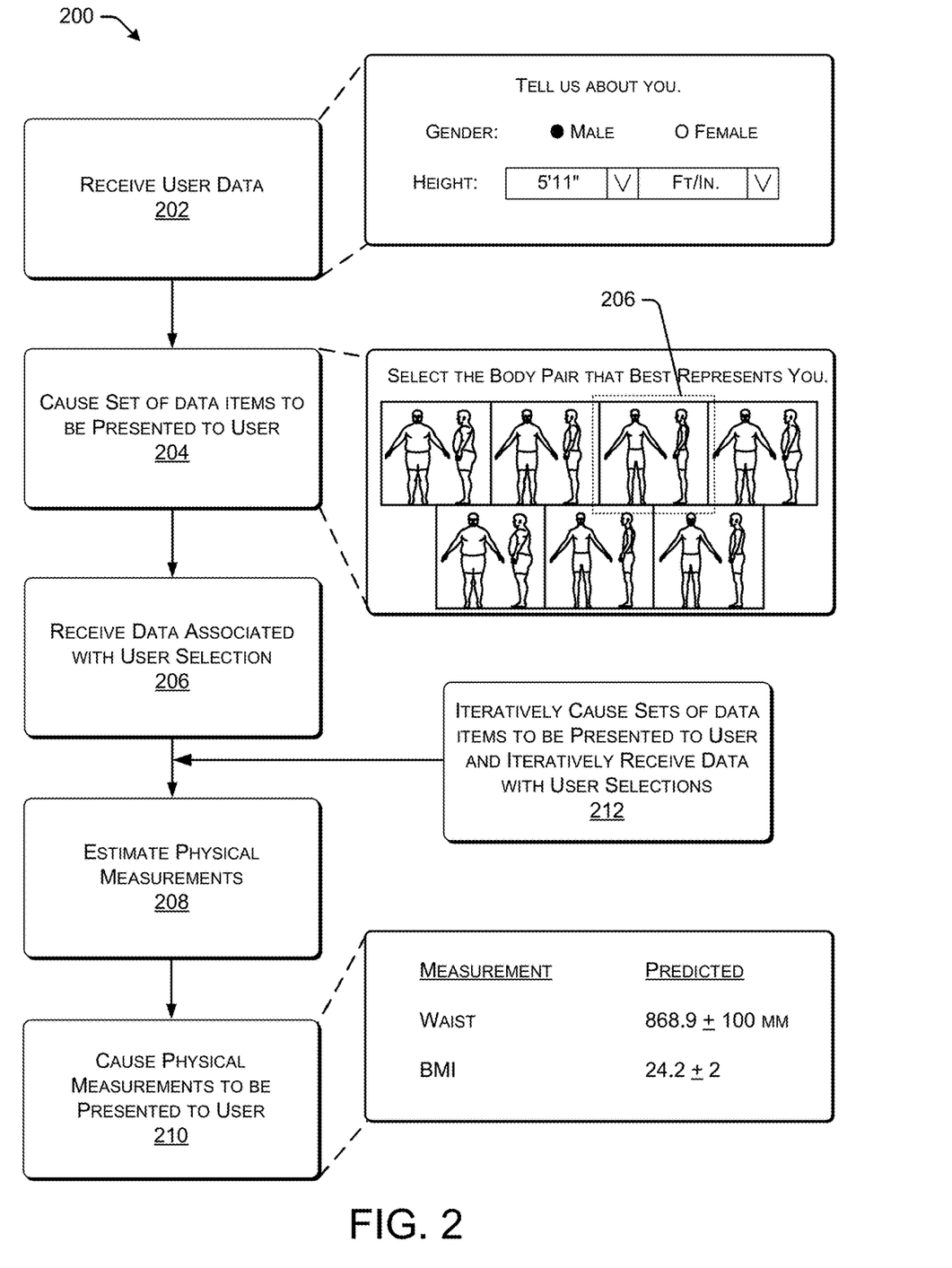
FIG. 2 is a flow diagram that illustrates an example process to estimate physical measurements utilizing data items associated with graphical elements representing human bodies that are presented to users.

FIG. 2 is a flow diagram that illustrates an example process 200 to estimate physical measurements utilizing data items 122 associated with one or more graphical elements 123A, 123B, etc. representing human bodies that are presented to users 106.

Block 202 illustrates receiving user data 118. The data collection module 116 can receive data (e.g., user data 118) associated with users 106 from the users 106 and/or on behalf of the users 106 and/or access data associated with users 106 via third party sources and systems (e.g., social networks, professional networks, etc.), as described above. In at least one example, the presentation module 126 can generate a user interface that prompts a user 106 to input his or her gender and height as illustrated in the user interface associated with block 202. Additional and/or alternative user interfaces can be presented for prompting the user 106 for additional and/or alternative information. The presentation module 126 can cause the user interface to be presented to a user 106 via a display 130 of a device 108, as described above. A user 106 can indicate whether he or she is a male or female, respectively, and select his or her height from one or more drop down menus.

The user interface associated with block 202 is an example of a user interface that can be presented to users 106 and any other presentation or configuration can be used. In FIG. 2, the user 106 has indicated that he is a male and is 5'11" tall. The data collection module 116 can send data associated with the user's input (e.g., gender, height, etc.) to the presentation module 126.

In some examples, process 200 can be executed without a user 106 indicating whether he or she is male or female, respectively, or specifying his or her height.

Block 204 illustrates causing a set of data items 134 to be presented to a user 106. In at least one example, the presentation module 126 can receive user data 118 from the data collection module 116 and, leveraging the index associated with the database 120 described above, the presentation module 126 can retrieve data items 122 and generate a user interface that includes a set of data items 134 associated with the user's input (e.g., gender, height, etc.). In an example, the set of data items 134 can represent a subset of data items 122 stored in the database 120 that represent human bodies having a same set of magnitudes with respect to every dimension except one dimension. That is, the set of data items 134 can include data items 122 that represent human bodies with different magnitudes associated with one dimension, but otherwise have the same set of magnitudes. In at least one example, based at least in part on receiving the input indicating the gender and height of the user, the presentation module 126 can access a predetermined number of data items 122 associated with the same gender and height as the user 106. The predetermined number can be determined on a number of data items 122 that can be arranged on a user interface, an arbitrary number, etc.

Each data item 122 in a set of data items 134 can be associated with one or more graphical elements that represent a human body with a different magnitude for a dimension than each of the other data items 122 in the set of data items 134. As a non-limiting example, each data item 122 in a set of data items 134 can be associated with one or more graphical elements that represent a male who is 5'11"; however, each data item 122 can be associated with one or more graphical elements that can represent a 5'11" male with a different waist measurement. In at least one example, each data item 122 can be associated with other magnitudes that are associated with standardized measurements associated with a population, as described below. For instance, each data item 122 can be associated with one or more graphical elements that represent a human body with a standardized BMI.

In additional and/or alternative examples, the set of data items 134 can represent a set of data items 134 stored in the database 120 that represent human bodies having a different sets of magnitudes with respect to different dimensions. For instance, in some examples, the presentation module 126 can retrieve data items 122 and generate a user interface that includes a set of data items 134 arranged in a matrix arrangement in which one axis is associated with BMI and the other axis is associated with waist measurement. That is, the data items 122 represent human bodies with different BMIs along one axis and the data items 122 represent human bodies with different waist measurements along the other axis. In other examples, the presentation module 126 can retrieve data items 122 and generate a user interface that includes a set of data items 134 with varying dimensions that can be presented in a pattern, a random configuration, etc. For instance, in at least one example, the set of data items 134 can include all of the data items 122 stored in the database 120 and the presentation module 126 can present all of the data items 122 to the user 106.

Block 206 illustrates receiving data associated with a user selection. A user 106 can interact with a user interface to indicate which data item 122 of the set of data items 134 is associated with at least one graphical element representing a human body that looks most similar to him or her, as described above. In at least some examples, users 106 can leverage zoom features to enlarge the individual data items 122. The device 108 can determine an input associated with the user selection. As a non-limiting example, box 206 indicates that the user selected the data item 122 within the box 206 as the pair of graphical elements 123A, 123B, etc. that are most representative of his body or of the body of another person. The device 108 can send data associated with the input to the data collection module 116. The data collection module 116 can receive the data and can analyze the input to determine the set of magnitudes associated with the data item 122 selected by the user 106. The data collection module 116 can send the data associated with the set of magnitudes to the measurement estimation module 124 and/or the presentation module 126.

Block 208 illustrates estimating physical measurements. The measurement estimation module 124 accesses user data 118 and receives and/or accesses the logs associated with the data indicating a selection of the data item 122 that represents at least one graphical element of a human body that best represents the user's 106 own body. In additional and/or alternative examples, the measurement estimation module 124 can access user data 118 and receive and/or access the logs associated with the data indicating a selection of the data item 122 that represents at least one graphical element of a human body that best represents a body of another person (e.g., a friend, a family member, a suspected criminal/person of interest, etc.), as described above. The measurement estimation module 124 can utilize a predictive model (e.g., Predictive Model 1, Predictive Model 2, etc.) to compute estimated physical measurements based at least in part on the user data 118 (e.g., gender, height, etc.) and the magnitudes associated with user selections of data items 122. In at least one example, the measurement estimation module 124 can estimate at least a waist measurement and/or BMI using a predictive model, like Predictive Models 1 and 2 described above.

Block 210 illustrates causing the physical measurements to be presented to the user 106. The presentation module 126 can generate a user interface that provides functionality to present estimated physical measurements to the user 106 via the display 130 of the device 108. The presentation module 126 can send the user interface to the device 108 for presenting the user interface to the user 106 on the display 130 of the device 108. An example user interface is associated with block 210. The user interface associated with block 210 is an example of a user interface that can be presented to users 106 and any other presentation or configuration can be used.

The physical measurements can be presented to the user 106 as finite physical measurements, ranges of physical measurements, physical measurements including a confidence interval, etc. As a non-limiting example, the physical measurements are presented as physical measurements including confidence intervals. For instance, the measurement estimation module 124 estimated the waist measurement of the user 106 represented in FIG. 2 as 868.9 millimeters with a confidence interval of ±100 millimeters. That is, the user's 106 waist is likely to measure 768.9-968.9 millimeters. One or more graphical representations can also be presented with the physical measurements to visually represent physical measurements associated with the user 106.

Block 212 illustrates iteratively causing sets of data items 134 to be presented to the user 106 and iteratively receiving data associated with the user selections. In at least some examples, based at least in part on receiving data associated with a first input, the presentation module 126 can receive and/or access data from the data collection module 116 that is associated with the magnitudes of the data item 122 selected by the user 106 and can leverage the index associated with the database 120 to retrieve a new set of data items 134. The new set of data items 134 can include a same number of data items 122 as the first set of data items 134, more data items 122, or fewer data items 122. The presentation module 126 can generate a user interface that includes the new set of data items 134 that are associated with one or more graphical elements that represent human bodies with at least some new magnitudes.

Data items 122 in the new set of data items 134 can each be associated with one or more graphical elements that represent human bodies with at least one magnitude associated with a dimension that is different from the other data items 122 in the new set of data items 134 but otherwise have the same magnitudes as the other data items 122 in the new set of data items 134 with respect to other dimensions. In some examples, at least one of the magnitudes associated with all of the data items 122 in the new set of data items 134 is determined based at least in part on a magnitude associated with the data item 122 selected by the user 106 in the first set of data items 134. The presentation module 126 can cause a user interface associated with the new set of data items 134 to be presented on a display 130 of a device 108, as described above.

In at least one example, based at least in part on receiving data associated with the first input indicating which data item 122 in a set of data items 134 is associated with at least one graphical element that represents a human body that best represents the user 106, the data collection module 114 can analyze the selection and determine the magnitudes associated with the data item 122 selected by the user 106. The data collection module 114 can log each of the inputs and associate the logs with the profile corresponding to the user 106 in the database associated with the user data 118 and/or other data repository. For instance, if the user 106 selected a data item 122 associated with a graphical element that represents a human body with a waist measurement of 35 inches, the data collection module 114 can associate that log the corresponds to the user selection with the user profile corresponding to the user 106.

Based at least in part on determining the magnitudes associated with the data item 122 selected by the user 106, the presentation module 126 can access a predetermined number of data items 122 that are associated with the same gender, height, and magnitude (e.g., waist measurement of 35 inches) to select a new set of data items 134. The new set of data items 134 can include data items 122 that are associated with graphical elements that represent human bodies that have different magnitudes associated with a different dimension than the data items 122 in the first set of data items 134.

As a non-limiting example, if the data items 122 of the first set of data items 134 are associated with one or more graphical elements that represent human bodies that each have a waist measurement, the data items 122 of the new set of data items 122 can be associated with one or more graphical elements that represent human bodies that are associated with one or more graphical elements that represent human bodies that each have a different BMI. As such, in the non-limiting example, the new set of data items 122 can be associated with graphical elements that represent human bodies that have a same gender, same height, waist measurement, and varying BMIs. Each data item 122 can be associated with at least one graphical element that represents a human body with a different magnitude for the new dimension (e.g., BMI). As a non-limiting example, every data item 122 in the new set of data items 134 can be associated with graphical elements that represent a male who is 5'11" with a waist measurement of 35 inches; however, each data item 122 can be associated with graphical elements that represent a 5'11" male with a waist measurement of 35 inches and a different BMI.

In at least one example, a new set of data items 134 can include at least one data item 122 that was in the first set of data items 134. For instance, as a non-limiting example, the first set of data items 134 can be associated with data items 122 associated with one or more graphical elements that represent human bodies that have a same gender, same height, same BMIs, and various waist measurements. The user can select a data item 122 associated with a graphical element representing a human body having a BMI of 26 and a waist measurement (e.g., 35 inches). Accordingly, the new set of data items 134 can be associated with data items 122 associated with one or more graphical elements representing a human body having a waist measurement of 35 inches and varying BMIs, including the BMI associated with the data items 122 in the first set of data items 134 (e.g., 26). Therefore, in at least one example, a data item 122 in an immediately preceding set of data items 134 can also be included in the new set of data items 134.

The presentation module 126 can iteratively define new sets of data items 134 to be presented to the user 106. As described above, each new set of data items 134 can be associated with data items 122 that are associated with one or more graphical elements that represent human bodies that have a different magnitude associated with a new dimension. The presentation module 126 can cause the sets of data items 134 to be presented to the user 106 via a user interface configured to receive input. Based at least in part on causing the sets of data items 134 to be presented to the user 106, the device 108 can determine inputs and send data corresponding to the inputs to the data collection module 114. The data collection module 114 can receive inputs indicating which data item 122 is associated with at least one graphical element that best represents the user 106. The measurement estimation module 124 can leverage the user data 118, including the data associated with the inputs, and the predictive model to estimate the physical measurements associated with the user 106, as described above. In some examples, the measurement estimation module 124 can leverage the user data 118, including the data associated with the inputs, and the predictive model to estimate the physical measurements associated with another person, as described above.

Figure 3:
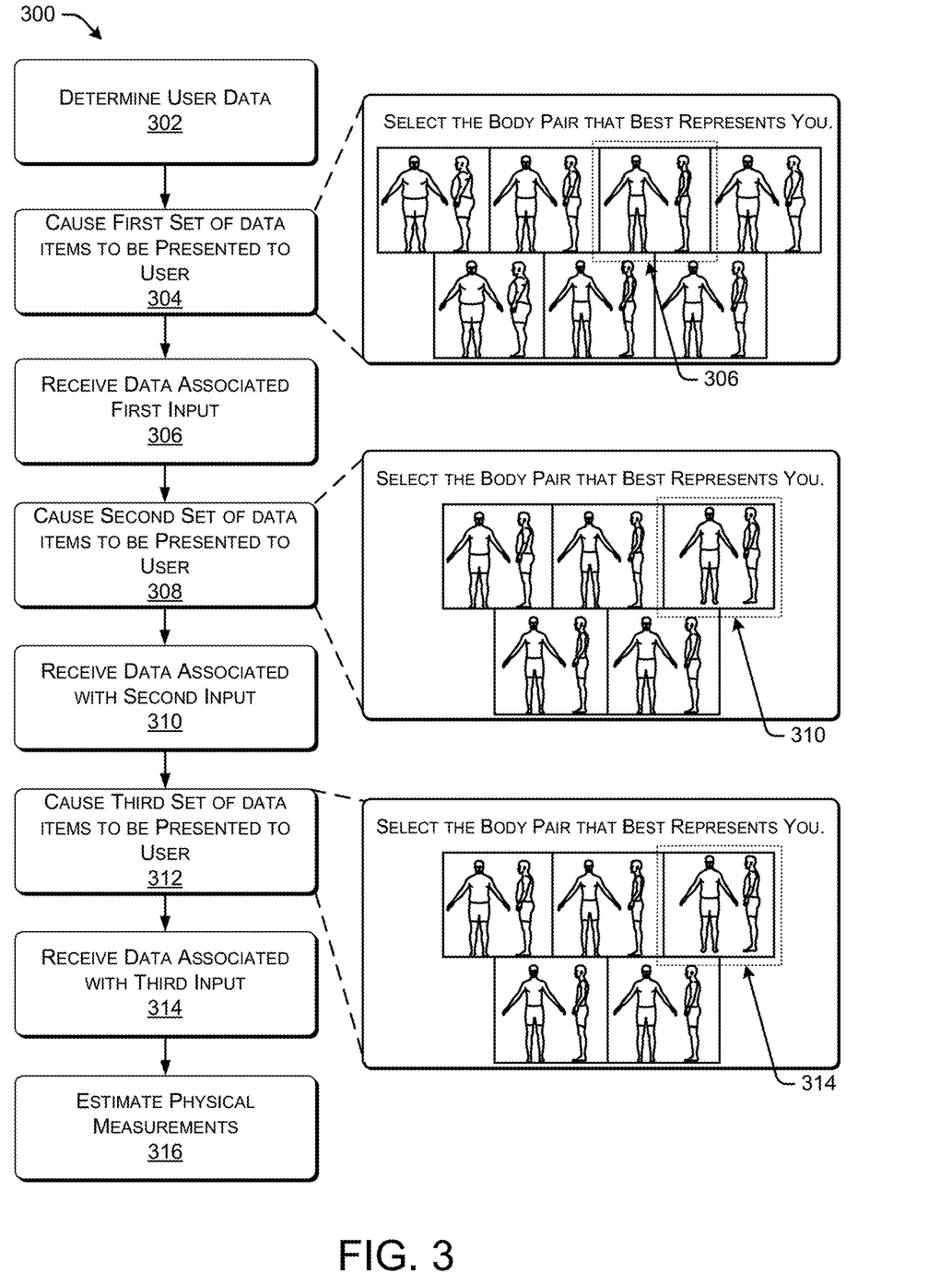
FIG. 3 is a flow diagram that illustrates another example process to estimate physical measurements utilizing data items associated with graphical elements representing human bodies that are presented to users.

FIG. 3 is a flow diagram that illustrates another example process 300 to estimate physical measurements utilizing data items 122 associated with graphical elements that represent human bodies that are presented to users 106.

Block 302 illustrates determining user data 118. The data collection module 116 can receive data associated with users 106 from the users 106 and/or on behalf of the user 106 and/or access data associated with users 106 via third party sources and systems (e.g., social networks, professional networks, etc.), as described above. In at least one example, the presentation module 126 can generate a user interface that prompts a user 106 for his or her gender, height measurement, and/or other dimensions, as described above.

Block 304 illustrates causing a first set of data items 122 to be presented to the user 106. In at least one example, the presentation module 126 can access user data 118 and can utilize the index associated with the database 120 to retrieve data items 122 associated with one or more graphical elements that represent human bodies with at least some of the same physical measurements as the user 106 (per the user data 118). The presentation module 126 can utilize the retrieved data items 122 to generate a user interface that includes a first set of data items 134. The user interface can be configured to receive user selection of one or more data items 122.

In at least one example, based at least in part on receiving the input indicating the gender and height of the user 106, the presentation module 126 can retrieve a predetermined number of data items 122 associated with graphical elements that represent human bodies that are associated with the same gender and height. Each data item 122 in the first set of data items 134 can be associated with one or more graphical elements that represent a human body with at least one different magnitude for a dimension and same magnitudes for each of the other dimensions.

As a non-limiting example, each data item 122 in the first set of data items 134 associated with block 304 can be associated with one or more graphical elements that represent a human body of the same gender and height, but each data item 122 can have a different waist measurement. In at least one example, each data item 122 can be associated with one or more graphical elements that represent human bodies that have a same predetermined BMI. In at least one example, the predetermined BMI can be a standardized BMI (e.g., average, median, etc.) for a population of users who have been previously measured. That is, each data item 122 can be associated with graphical elements that represent human bodies with a gender and a height that are the same as the user 106, a same predetermined BMI, and a different waist measurement.

Block 306 illustrates receiving data associated with a first input. A user 106 can interact with a user interface to indicate which data item 122 of the first set of data items 134 is associated with one or more graphical elements that look most similar to him or her. As described above, in some examples, a user 106 can interact with a user interface to indicate which data item 122 of the second set of data items 134 is associated with one or more graphical elements that look most similar to another person (e.g., a friend, a family member, a suspected criminal/person of interest, etc.).

As a non-limiting example, box 306 indicates that the user 106 selected the data item 122 within the box 306 as the data item 122 associated with graphical elements most representative of his body. The device 108 can determine the selection and can send data corresponding to the input to the data collection module 116. The data collection module 116 can receive the data associated with the first input and can determine the magnitudes associated with the data item 122 selected by the user 106 in the first input. The data collection module 116 can log the first input and associate the log with the user profile corresponding to the user 106. The data collection module 116 can send data associated with the first input (e.g., the magnitudes associated with the data item 122 selected by the user 106) to the presentation module 126.

Block 308 illustrates causing a second set of data items 134 to be presented to the user 106. As described above, the presentation module 128 can iteratively cause additional sets of data items 134 to be presented to the user 106. In at least one example, based at least in part on receiving the first input 306 indicating which data item 122 is associated with one or more graphical elements that best represent the user 106, the data collection module 114 can analyze the selection and determine the magnitudes associated with the data item 122 selected by the user 106, as described above. The presentation module 126 can receive data associated with the input 306 (e.g., the magnitudes associated with the data item 122 selected by the user 106) and can utilize the data and the index associated with the database 120 to access a predetermined number of data items 122 that represent human bodies having the same gender, height, and set of magnitudes, with the exception of magnitudes associated with one dimension. The second set of data items 134 can be associated with one or more graphical elements that represent human bodies that have different magnitudes associated with a different dimension than the first set of data items 134.

As a non-limiting example, if the data items 122 in the first set of data items 122 are associated with one or more graphical elements that represent human bodies that have different waist measurements, the data items 122 in the second set of data items 134 can be associated with one or more graphical elements that represent human bodies that have a different BMI. Each data item 122 can represent a human body with a different magnitude for the dimension. For instance, each data item 122 can be associated with one or more graphical elements that represent a human body with a height and gender that is the same as the user 106, a waist measurement that corresponds to the waist measurement associated with the previously selected data item 122, and a different BMI. In some examples, as described above, one of the data items 122 in the second set of data items 134 can have a same BMI as the data item 122 selected in the first set of data items 134.

Block 310 illustrates receiving data associated with a second input from the user 106. A user 106 can interact with a user interface to indicate which data item 122 of the second set of data items 134 is associated with one or more graphical elements that look most similar to him or her. As described above, in some examples, a user 106 can interact with a user interface to indicate which data item 122 of the second set of data items 134 is associated with one or more graphical elements that look most similar to another person (e.g., a friend, a family member, a suspected criminal/person of interest, etc.).

As a non-limiting example, the box 310 indicates that the user 106 selects the data item within the box 310 as the data item associated with one or more graphical elements that are most representative of his body. The device 108 can determine the user selection and can send data associated with the second input to the data collection module 116. The data collection module 116 can receive the data associated with the second input and can determine the magnitude associated with the data item 122 selected by the user 106. The data collection module 116 can log the second input and associate the log with the user 106 in the user data 118. The data collection module 116 can send data associated with the second input (e.g., the magnitudes associated with the data item 122 selected by the user 106) to the presentation module 126.

Block 312 illustrates causing a third set of data items 134 to be presented to the user 106. As described above, the presentation module 128 can iteratively cause additional sets of data items 134 to be presented to the user 106. In at least one example, based at least in part on receiving data associated with the second input indicating data item 122 is associated with one or more graphical elements that best represent the user 106, the data collection module 114 can analyze the selection and determine the magnitudes associated with the data item 122 selected by the user 106, as described above. The presentation module 126 can receive data associated with the second input (e.g., the magnitudes associated with the data item 122 selected by the user 106) and can utilize the data and the index associated with the database 120 to access a predetermined number of data items 122 that are associated with one or more graphical elements that represent human bodies having the same gender, height, and set of magnitudes, with the exception of magnitudes associated with one dimension. The third set of data items 134 can be associated with one or more graphical elements that represent human bodies that have different magnitudes associated with a different dimension than the first set and/or second set of data items 134.

As a non-limiting example, if the second set of data items 134 are associated with one or more graphical elements that represent human bodies that have a different BMI, the third set of data items 134 can be associated with one or more graphical elements that represent human bodies that have a different waist measurement and/or other magnitude associated with another dimension. Each data item 122 can be associated with one or more graphical elements that represent a human body with a different magnitude for the dimension. For instance, data item 122 can be associated with one or more graphical elements that represent a human body with a height and gender that is the same as the user 106, a BMI that corresponds to the BMI associated with the previously selected graphical element 122, and different waist measurements (or other dimension).

Block 314 illustrates receiving data associated with a third input. A user 106 can interact with a user interface to indicate which data item 122 of the third set of data items 134 is associated with one or more graphical elements that look most similar to him or her. As described above, in some examples, a user 106 can interact with a user interface to indicate which data item 122 of the second set of data items 134 is associated with one or more graphical elements that look most similar to another person (e.g., a friend, a family member, a suspected criminal/person of interest, etc.).

As a non-limiting example, the box 314 indicates that the user 106 selects the data item 122 within the box 314 as the data item 126 associated with one or more graphical elements that are most representative of his body. The device 108 can determine the user selection and can send data associated with the third input to the data collection module 116. The data collection module 116 can receive the third input and can determine the magnitudes associated with the data item 122 selected by the user 106. The data collection module 116 can log the third input and associate the log with the user 106 in the user data 118. The data collection module 116 can send data associated with the third input (e.g., the magnitudes associated with the data item 122 selected by the user 106) to the measurement estimation module 124.

Block 316 illustrates estimating physical measurements associated with the user 106 or the other person, as described above. The measurement estimation module 124 accesses user data 118 including inputs indicating a selection of at least one data item 122 associated with one or more graphical elements that best represents the user's 106 body. In additional and/or alternative examples, the measurement estimation module 124 can access user data 118 including inputs indicating a selection of at least one data item 122 associated with one or more graphical elements that best represents another person's body. The measurement estimation module 124 can utilize a predictive model (e.g., Predictive Model 1, Predictive Model 2, etc.) to compute estimated physical measurements based at least in part on the user data 118 (e.g., user gender, height, etc.) and the inputs. In at least one example, the measurement estimation module 124 can estimate at least a waist measurement and/or BMI using a predictive model like the predictive models described above.

Process 300 includes three iterations of causing sets of data items 122 to be presented to users 106 and receiving data associated with inputs, but any number of iterations can be used to estimate physical measurements. In some examples, the data collection module 116 can receive data associated with inputs following each presentation of a set of data items 134 and can subsequently send the data associated with each input to the measurement estimation module 124. In other examples, after the last iteration, the data collection module 116 can receive data associated with a last input (e.g., the magnitudes associated with the last data item 122 selected by the user 106) and can subsequently send the data to the measurement estimation module 124 for estimating the physical measurements.

Figure 4:
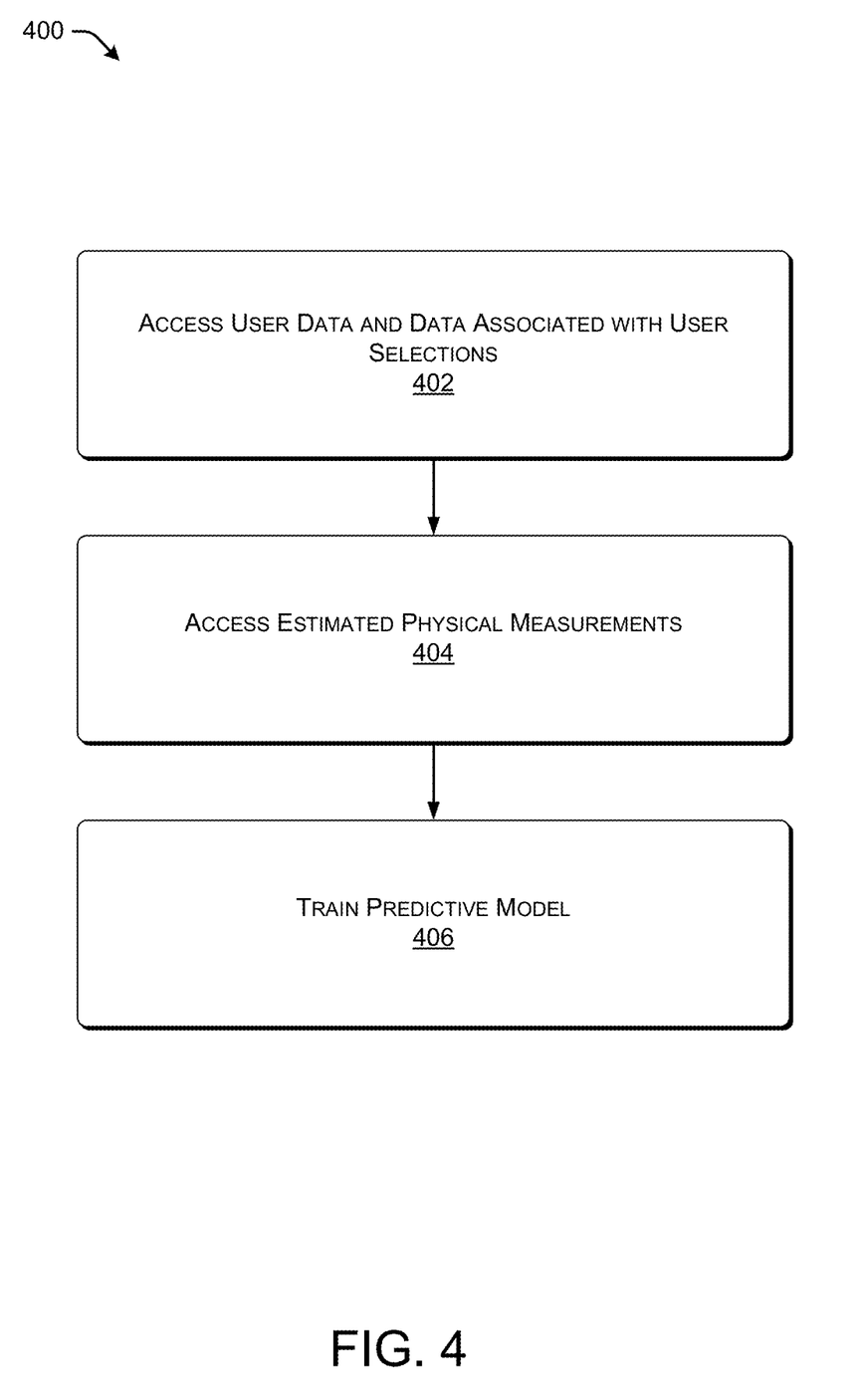
FIG. 4 is a flow diagram that illustrates an example process to train a predictive model for estimating physical measurements.

FIG. 4 is a flow diagram that illustrates an example process 400 to train a predictive model.

Block 402 illustrates accessing user data 118 and data associated with inputs. The training module 128 can receive and/or access user data 118 from the data collection module 116. In at least one example, the training module 128 can access determined physical measurements associated with users 106 (i.e., physical measurements ascertained by measurement devices). Additionally, the training module 128 can access data associated with inputs associated with users 106. As described above, the inputs can be associated with user selections of data items 122 from each set of data items 134 caused to be presented to the user 106. The determined physical measurements and the data associated with the inputs can be associated with profiles corresponding to the users 106 and stored in the database associated with the user data 118 and/or some other data repository associated with the user data 118.

Block 404 illustrates accessing estimated physical measurements. The training module 128 can access the estimated physical measurements determined by the measurement estimation module 124. The estimated physical measurements can also be associated with each individual user 106 and/or the determined physical measurements and data associated with the inputs.

Block 406 illustrates training predictive models. The training module 128 can leverage machine learning algorithms (e.g., supervised learning, unsupervised learning, semi-supervised learning, deep learning, etc.) to learn predictive models. The measurement estimation module 124 can leverage the predictive models to estimate physical measurements based at least in part on one or more determined physical measurements and the inputs. Predictive Model 1 and Predictive Model 2, described above, are examples of predictive models learned using the machine learning algorithms.

Example Clauses

A. A computer-implemented method for estimating physical measurements associated with users based at least in part on generating personalized user interfaces that provide functionality for receiving user input, the computer-implemented method comprising: accessing a database storing a plurality of data items; causing a set of data items of the plurality of data items to be presented to a user via a user interface that is presented on a display of a device associated with the user, wherein first individual data items in the set of data items are associated with at least one graphical element representing a human body with individual magnitudes corresponding to individual dimensions of a plurality of dimensions; receiving first data from the device, the first data indicating a selection of a first individual data item from the first individual data items, the first individual data item being associated with a first individual magnitude of the individual magnitudes associated with a first dimension of the plurality of dimensions and a second individual data item being associated with a second individual magnitude of the individual magnitudes associated with a second dimension of the plurality of dimensions; and estimating physical measurements associated with the user based at least in part on at least one of the first individual magnitude or the second individual magnitude.

B. A computer-implemented method as paragraph A recites, further comprising: based at least in part on receiving the first data, causing an additional set of data items of the plurality of data items to be presented to the user via the user interface, wherein second individual data items in the additional set of data items are associated with at least an additional graphical element representing the human body with the second individual magnitude and third individual magnitudes of the individual magnitudes associated with a third dimension of the plurality of dimensions; receiving second data from the device, the second data indicating an additional selection of a second individual data item from the second individual data items, the second individual data item being associated with a third individual magnitude of the third individual magnitudes; and estimating the physical measurements associated with the user further based at least in part on the third individual magnitude.

C. A computer-implemented method as paragraph B recites, wherein the third dimension corresponds to the first dimension.

D. A computer-implemented method as paragraph C recites, wherein at least one data item in the additional set of data items comprises the first individual data item.

E. A computer-implemented method as any of paragraphs A-D recite, wherein: the first dimension corresponds to a body mass index measurement; the second dimension corresponds to a waist measurement; and estimating the physical measurements comprises estimating a body mass index measurement of the user and a waist measurement of the user.

F. A computer-implemented method as any of paragraphs A-E recite, wherein individual data items of the plurality of data items stored in the database are associated with graphical elements representing the human body that correspond to a same height and a same gender as the user.

G. A computer-implemented method as any of paragraphs A-F recite, wherein the estimating the physical measurements associated with the user comprises estimating the physical measurements further based at least in part on a multiple regression predictive model.

H. A computer-implemented method as any of paragraphs A-G recite, wherein: individual data items of the plurality of data items in the database are associated with two graphical elements representing the human body; and each graphical element of the two graphical elements corresponds to a different view of the human body.

I. A computer-implemented method as any of paragraphs A-H recite, further comprising: generating an additional user interface that provides functionality to present the physical measurements to the user via the display of the device; and sending the additional user interface to the device.

J. One or more computer-readable media encoded with instructions that, when executed by a processor, configure a computer to perform a method as any of paragraphs A-I recite.

K. A device comprising one or more processors and one or more computer readable media encoded with instructions that, when executed by the one or more processors, configure a computer to perform a computer-implemented method as any of paragraphs A-I recite.

L. A computer-implemented method for estimating physical measurements associated with users based at least in part on generating personalized user interfaces that provide functionality for receiving user input, the computer-implemented method comprising: means for accessing a database storing a plurality of data items; means for causing a set of data items of the plurality of data items to be presented to a user via a user interface that is presented on a display of a device associated with the user, wherein first individual data items in the set of data items are associated with at least one graphical element representing a human body with individual magnitudes corresponding to individual dimensions of a plurality of dimensions; means for receiving first data from the device, the first data indicating a selection of a first individual data item from the first individual data items, the first individual data item being associated with a first individual magnitude of the individual magnitudes associated with a first dimension of the plurality of dimensions and a second individual data item being associated with a second individual magnitude of the individual magnitudes associated with a second dimension of the plurality of dimensions; and means for estimating physical measurements associated with the user based at least in part on at least one of the first individual magnitude or the second individual magnitude.

M. A computer-implemented method as paragraph L recites, further comprising: based at least in part on receiving the first data, means for causing an additional set of data items of the plurality of data items to be presented to the user via the user interface, wherein second individual data items in the additional set of data items are associated with at least an additional graphical element representing the human body with the second individual magnitude and third individual magnitudes of the individual magnitudes associated with a third dimension of the plurality of dimensions; means for receiving second data from the device, the second data indicating an additional selection of a second individual data item from the second individual data items, the second individual data item being associated with a third individual magnitude of the third individual magnitudes; and means for estimating the physical measurements associated with the user further based at least in part on the third individual magnitude.

N. A computer-implemented method as paragraph M recites, wherein the third dimension corresponds to the first dimension.

O. A computer-implemented method as paragraph N recites, wherein at least one data item in the additional set of data items comprises the first individual data item.

P. A computer-implemented method as any of paragraphs L-0 recite, wherein: the first dimension corresponds to a body mass index measurement; the second dimension corresponds to a waist measurement; and estimating the physical measurements comprises means for estimating a body mass index measurement of the user and a waist measurement of the user.

Q. A computer-implemented method as any of paragraphs L-P recite, wherein individual data items of the plurality of data items stored in the database are associated with graphical elements representing the human body that correspond to a same height and a same gender as the user.

R. A computer-implemented method as any of paragraphs L-Q recite, wherein the estimating the physical measurements associated with the user comprises means for estimating the physical measurements further based at least in part on a multiple regression predictive model.

S. A computer-implemented method as any of paragraphs L-R recite, wherein: individual data items of the plurality of data items in the database are associated with two graphical elements representing the human body; and each graphical element of the two graphical elements corresponds to a different view of the human body.

T. A computer-implemented method as any of paragraphs L-S recite, further comprising: means for generating an additional user interface that provides functionality to present the physical measurements to the user via the display of the device; and means for sending the additional user interface to the device.

U. A system comprising: one or more processors; memory; and one or more modules stored in the memory and executable by the one or more processors to perform operations comprising: generating a user interface for presenting a first set of data items of a plurality of data items to a user, wherein first individual data items in the first set of data items represent human bodies having at least first magnitudes of a set of magnitudes associated with first dimensions and second magnitudes of the set of magnitudes associated with second dimensions; receiving data indicating a selection of a first individual data item of the first individual data items; computing estimated physical measurements associated with the user based at least in part on the selection; and generating a second user interface for presenting the estimated physical measurements to the user.

V. The system as paragraph U recites, wherein the operations further comprise, determining, based at least in part on the selection of the first individual data item, a first magnitude of the first magnitudes represented by the first individual data item and a second magnitude of the second magnitudes represented by the first individual data item.

W. The system as paragraph V recites, wherein: the operations further comprise based at least in part on receiving the data, generating at least one additional user interface for presenting an additional set of data items of the plurality of data items to the user; second individual data items in the additional set of data items are associated with the first magnitude or the second magnitude; and the second individual data items are each associated with a different magnitude associated with a third magnitude of the set of magnitudes associated with a third dimension.

X. The system as paragraph W recites, wherein the operations further comprise: receiving additional data indicating an additional selection of a second individual data item from the second individual data items; and computing the estimated physical measurements further based at least in part on the additional selection.

Y. A first device comprising: one or more processors; memory; and one or more modules stored in the memory and executable by the one or more processors to perform operations comprising: causing a first user interface of a first set of data items to be presented to a user associated with the first device, wherein first individual data items in the first set of data items represent human bodies having at least first magnitudes associated with a first dimension and second magnitudes associated with a second dimension, wherein individual second magnitudes of the second magnitudes are different for each first individual data item of the first individual data items; determining a first input indicating a first selection of a first individual data item of the first individual data items, wherein the first individual data item is associated with an individual second magnitude of the individual second magnitudes; sending first data corresponding to the first input to a second device; receiving second data from the second device, the second data corresponding to estimated physical measurements determined based in part on the individual second magnitude; and causing a data item corresponding to the estimated physical measurements to be presented to the user via the first device.

Z. A first device as paragraph Y recites, wherein the first magnitudes associated with first dimensions correspond to a standardized measurement associated with a population of previously measured users.

AA. A first device as any of paragraphs Y or Z recite, wherein the operations further comprise: based at least in part on sending the first data, causing a second user interface of a second set of data items to be presented to the user, wherein second individual data items in the second set of data items represent human bodies having the second magnitude and third magnitudes associated with a third dimension, wherein individual third magnitudes of the third magnitudes are different for each second individual data item of the second individual data items; determining a second input indicating a second selection of a second individual data item of the second individual data items, wherein the second individual data item is associated with an individual third magnitude of the individual third magnitudes; sending third data corresponding to the second input to the second device; and receiving the second data from the second device, the second data corresponding to the estimated physical measurements further determined based in part on the individual second magnitude and the individual third magnitude.

AB. A first device as paragraph AA recites, wherein the third dimension corresponds to the first dimension.

AC. A first device as paragraph AA recites, wherein the operations further comprise: based at least in part on sending the third data, causing a third user interface of a third set of data items to be presented to the user, wherein third individual data items in the third set of data items represent human bodies having the third magnitude and fourth magnitudes associated with a fourth dimension, wherein individual fourth magnitudes of the fourth magnitudes are different for each third individual data item of the third individual data items; determining a third input indicating a third selection of a third individual data item of the third individual data items, wherein the third individual data item is associated with an individual fourth magnitude of the individual fourth magnitudes; sending fourth data corresponding to the third input to the second device; and receiving the second data from the second device, the second data corresponding to the estimated physical measurements further determined based in part on the individual second magnitude, the individual third magnitude, and the individual fourth magnitude.

AD. A first device as paragraph AC recites, wherein the fourth dimension corresponds to the second dimension.

AE. A first device as paragraph AC recites, wherein: the first dimension and the third dimension correspond to a body mass index measurement; the second dimension and the fourth dimension correspond to a waist measurement; and the estimated physical measurements include an estimated body mass index measurement and an estimated waist measurement.

Conclusion

Although the subject matter has been described in language specific to structural features and/or methodological acts, it is to be understood that the subject matter defined in the appended claims is not necessarily limited to the specific features or acts described. Rather, the specific features and acts are described as illustrative forms of implementing the claims.

Conditional language such as, among others, "can," "could," "might" or "can," unless specifically stated otherwise, are understood within the context to present that certain examples include, while other examples do not necessarily include, certain features, elements and/or steps. Thus, such conditional language is not generally intended to imply that certain features, elements and/or steps are in any way required for one or more examples or that one or more examples necessarily include logic for deciding, with or without input or prompting, whether certain features, elements and/or steps are included or are to be performed in any particular example Conjunctive language such as the phrase "at least one of X, Y or Z," unless specifically stated otherwise, is to be understood to present that an item, term, etc. can be either X, Y, or Z, or a combination thereof.

What is claimed is:

1. A computer-implemented method for creating realistic avatars based on estimated physical measurements of a body of a user, the method comprising:
   accessing a database storing a plurality of data items, wherein each data item is associated with at least one graphical element representing a human body with individual magnitudes corresponding to individual dimensions of a plurality of dimensions;
   performing the following for a plurality of iterations:
      causing a set of data items of the plurality of data items to be presented to the user via a user interface that is presented on a display of a device associated with the user, wherein individual data items in the set of data items are associated with the at least one graphical element representing the human body with individual magnitudes corresponding to individual dimensions of the plurality of dimensions;
      receiving data from the device, the data indicating a user selection of an individual data item from the individual data items, the individual data item being associated with a particular individual magnitude of the individual magnitudes associated with a particular dimension of the plurality of dimensions; and
      determining a subsequent set of data items of the plurality of data items to be presented to the user via the user interface based on the user selection of the individual data item, wherein individual data items in the subsequent set of data items are associated with the at least one graphical element representing the human body with a different individual magnitudes corresponding to a respective individual dimension of the plurality of dimensions;
   estimating physical measurements associated with the user based on the different individual magnitudes corresponding to the respective individual dimension of the plurality of dimensions and a predictive model, the predictive model trained based on user selections of data items from each set of data items caused to be presented to the user and estimated physical measurements associated with profiles corresponding to users; and
   generating an avatar for the user based on the estimated physical measurements associated with the user.

2. The computer-implemented method according to claim 1,
   wherein a first dimension of the plurality of dimensions corresponds to a body mass index measurement,
   wherein a second dimension of the plurality of dimensions corresponds to a waist measurement, and
   wherein estimating the physical measurements comprises estimating a body mass index measurement of the user and a waist measurement of the user.

3. The computer-implemented method according to claim 1, wherein individual data items of the plurality of data items stored in the database are associated with graphical elements representing the human body that correspond to a same height and a same gender as the user.

4. The computer-implemented method according to claim 1, wherein the predictive model predicts at least one physical measurement of the physical measures and includes weights that are based on training the respective predictive model using the plurality of data items stored in the database.

5. The computer-implemented method according to claim 1, further comprising:
   accessing user selections of data items from each set of data items caused to be presented to the user;
   accessing estimated physical measurements associated with profiles corresponding to users; and
   training the multiple regression model based on the user selections of data items from each set of data items caused to be presented to the user and estimated physical measurements associated with profiles corresponding to users.

6. The computer-implemented method according to claim 1,
   wherein individual data items of the plurality of data items in the database are associated with two graphical elements representing the human body, and
   wherein each graphical element of the two graphical elements corresponds to a different view of the human body.

7. The computer-implemented method according to claim 1, further comprising:
   generating an additional user interface that provides functionality to present the physical measurements and the avatar to the user via the display of the device; and
   sending the additional user interface to the device.

8. A system for creating realistic avatars based on estimated physical measurements of a body of a user, the system including:
   a data storage device that stores instructions for creating realistic avatars based on estimated physical measurements of a body of a user; and
   a processor configured to execute the instructions to perform a method including:
      accessing a database storing a plurality of data items, wherein each data item is associated with at least one graphical element representing a human body with individual magnitudes corresponding to individual dimensions of a plurality of dimensions;

performing the following for a plurality of iterations:

causing a set of data items of the plurality of data items to be presented to the user via a user interface that is presented on a display of a device associated with the user, wherein individual data items in the set of data items are associated with the at least one graphical element representing the human body with individual magnitudes corresponding to individual dimensions of the plurality of dimensions;

receiving data from the device, the data indicating a user selection of an individual data item from the individual data items, the individual data item being associated with a particular individual magnitude of the individual magnitudes associated with a particular dimension of the plurality of dimensions; and determining a subsequent set of data items of the plurality of data items to be presented to the user via the user interface based on the user selection of the individual data item, wherein individual data items in the subsequent set of data items are associated with the at least one graphical element representing the human body with a different individual magnitudes corresponding to a respective individual dimension of the plurality of dimensions;

estimating physical measurements associated with the user based on the different individual magnitudes corresponding to the respective individual dimension of the plurality of dimensions and a predictive model, the predictive model trained based on user selections of data items from each set of data items caused to be presented to the user and estimated physical measurements associated with profiles corresponding to users; and generating an avatar for the user based on the estimated physical measurements associated with the user.

9. The system according to claim 8,
wherein a first dimension of the plurality of dimensions corresponds to a body mass index measurement,
wherein a second dimension of the plurality of dimensions corresponds to a waist measurement, and
wherein estimating the physical measurements comprises estimating a body mass index measurement of the user and a waist measurement of the user.

10. The system according to claim 8, wherein individual data items of the plurality of data items stored in the database are associated with graphical elements representing the human body that correspond to a same height and a same gender as the user.

11. The system according to claim 8, wherein the predictive model predicts at least one physical measurement of the physical measures and includes weights that are based on training the respective multiple regression predictive model using the plurality of data items stored in the database.

12. The system according to claim 8, further comprising:
accessing user selections of data items from each set of data items caused to be presented to the user;
accessing estimated physical measurements associated with profiles corresponding to users; and
training the multiple regression models based on the user selections of data items from each set of data items caused to be presented to the user and estimated physical measurements associated with profiles corresponding to users.

13. The system according to claim 8,
wherein individual data items of the plurality of data items in the database are associated with two graphical elements representing the human body, and
wherein each graphical element of the two graphical elements corresponds to a different view of the human body.

14. The system according to claim 8, wherein the processor is further configured to execute the instructions to perform the method including:
generating an additional user interface that provides functionality to present the physical measurements and the avatar to the user via the display of the device; and
sending the additional user interface to the device.

15. One or more computer storage media storing instructions that, when executed by a computer, cause the computer to perform a method for creating realistic avatars based on estimated physical measurements of a body of a user, the method including:
accessing a database storing a plurality of data items, wherein each data item is associated with at least one graphical element representing a human body with individual magnitudes corresponding to individual dimensions of a plurality of dimensions;
performing the following for a plurality of iterations:
causing a set of data items of the plurality of data items to be presented to the user via a user interface that is presented on a display of a device associated with the user, wherein individual data items in the set of data items are associated with the at least one graphical element representing the human body with individual magnitudes corresponding to individual dimensions of the plurality of dimensions;
receiving data from the device, the data indicating a user selection of an individual data item from the individual data items, the individual data item being associated with a particular individual magnitude of the individual magnitudes associated with a particular dimension of the plurality of dimensions; and
determining a subsequent set of data items of the plurality of data items to be presented to the user via the user interface based on the user selection of the individual data item, wherein individual data items in the subsequent set of data items are associated with the at least one graphical element representing the human body with a different individual magnitudes corresponding to a respective individual dimension of the plurality of dimensions;
estimating physical measurements associated with the user based on the different individual magnitudes corresponding to the respective individual dimension of the plurality of dimensions and a predictive model, the predictive model trained based on user selections of data items from each set of data items caused to be presented to the user and estimated physical measurements associated with profiles corresponding to users; and
generating an avatar for the user based on the estimated physical measurements associated with the user.

16. The one or more computer storage media according to claim 15,
wherein a first dimension of the plurality of dimensions corresponds to a body mass index measurement, wherein a second dimension of the plurality of dimensions corresponds to a waist measurement, and wherein estimating the physical measurements comprises estimating a body mass index measurement of the user and a waist measurement of the user.

17. The one or more computer storage media according to claim 15, wherein individual data items of the plurality of data items stored in the database are associated with graphical elements representing the human body that correspond to a same height and a same gender as the user.

18. The one or more computer storage media according to claim 15, wherein the predictive model predicts at least one physical measurement of the physical measures and includes weights that are based on training the respective predictive model using the plurality of data items stored in the database.

19. The one or more computer storage media according to claim 15, further comprising:

accessing user selections of data items from each set of data items caused to be presented to the user;

accessing estimated physical measurements associated with profiles corresponding to users; and training the multiple regression models based on the user selections of data items from each set of data items caused to be presented to the user and estimated physical measurements associated with profiles corresponding to users.

20. The one or more computer storage media according to claim 15, wherein individual data items of the plurality of data items in the database are associated with two graphical elements representing the human body, and wherein each graphical element of the two graphical elements corresponds to a different view of the human body.

* * * * *